United States Patent
Boehm

(10) Patent No.: US 7,280,874 B2
(45) Date of Patent: Oct. 9, 2007

(54) METHODS FOR DETERMINING THERAPEUTIC RESONANT FREQUENCIES

(76) Inventor: Charlene A. Boehm, 320 Gilbert Rd., Columbus, NC (US) 28722

( * ) Notice: Subject to any disclaimer, the term of this patent is extended or adjusted under 35 U.S.C. 154(b) by 773 days.

(21) Appl. No.: 09/780,901

(22) Filed: Feb. 9, 2001

(65) Prior Publication Data

US 2007/0128590 A1    Jun. 7, 2007

Related U.S. Application Data

(60) Provisional application No. 60/181,460, filed on Feb. 10, 2000.

(51) Int. Cl.
*A61N 5/00* (2006.01)
*G01N 23/02* (2006.01)
*C12Q 1/68* (2006.01)

(52) U.S. Cl. .................... 607/100; 435/6; 436/58; 436/63; 702/19

(58) Field of Classification Search .............. 514/1, 514/2; 702/19; 703/11
See application file for complete search history.

(56) References Cited

U.S. PATENT DOCUMENTS

| | | | |
|---|---|---|---|
| 3,876,373 | A | 4/1975 | Glyptis |
| 4,524,079 | A | 6/1985 | Hofmann |
| 5,091,152 | A | 2/1992 | Thomas, Sr. |
| 5,326,446 | A | 7/1994 | Binger |
| 5,552,274 | A | 9/1996 | Oyama et al. |
| 5,556,418 | A | 9/1996 | Pappas |
| 5,658,322 | A | 8/1997 | Fleming |
| 5,676,695 | A | 10/1997 | Di Mino et al. |
| 5,690,692 | A | 11/1997 | Fleming |
| 5,891,182 | A | 4/1999 | Fleming |
| 5,908,441 | A | 6/1999 | Bare |
| 6,004,257 | A | 12/1999 | Jacobson |
| 6,060,293 | A | 5/2000 | Bohr et al. |
| 6,060,327 | A * | 5/2000 | Keen ................ 204/403.14 |
| 6,221,094 | B1 | 4/2001 | Bare |
| 6,310,179 | B1 * | 10/2001 | Batz et al. ............ 530/333 |

FOREIGN PATENT DOCUMENTS

| WO | WO 84/03165 | 8/1884 |
|---|---|---|
| WO | WO 93/24645 | 12/1993 |
| WO | WO 00/15097 A3 | 3/2000 |

OTHER PUBLICATIONS

BIOCHEMISTRY, by Lehninger [Worth Publishers, Inc., 70 Fifth Avenue, New York, New York 10011] (1970), pp. 638-646.*

The A.R.R.L. Antenna Book [The American Radio Relay League, Inc., Newington 11, Connecticut ] (1960), pp. 25-66.*
Definition of "oncogene" found at ww.http://m-w.com/dictionary/oncogene. Printed Dec. 10, 2006.*
Edwards, G.S. et al., Microwave-Field-Driven Acoustic-Modes in DNA, 47 BIOPHYS. J. 799, Jun. 1985.
Alexjander, S., The Infrared Frequencies of DNA Bases: Science and Art—Connecting with Our Bodies through "Molecular Music". *IEEE Engineering in Medicine and Biology*, pp. 74-79, Mar./Apr. 1999.
Cominole, B., Clinical Impressions and Speculations on the Use of High-Frequency Pulsed Energy, Paper presented at symposium given by The Dr. Abraham J. Ginsberg Foundation for medical research on Jun. 29, 1959.
Cutnell, J.D. et al., The Electromagnetic Spectrum, in Physics, second ed., p. 698, John Wiley & Sons, 1992.
Edwards, G. S. et al., Resonant Microwave Absorption of Selected DNA Molecules, *Physical Review Letters*, vol. 53, No. 13, pp. 1284-1287, Sep. 28, 1984.
Fleming, H., Effect of High-Frequency Fields on Micro-Organisms, Essential substance of a paper, "A Study of the Effect of High-Frequency Fields on Micro-Organisms," presented at a joint meeting on the Portland (Oreg.) Section and the Oregon State College Branch, Corballis, May 16, 1942, www.rife.org/hflem.htm.
Fröhlich, H., Long-Range Coherence and Energy Storage in Biological Systems, *International Journal of Quantum Chemistry*, vol. II, pp. 641-649, 1968.
Ginsberg, A. J., Pulsed Short Waves in the Treatment of Bursitis with Calcification, presented at the 36th Annual Meeting of the American Congress Of Physical Medicine And Rehabilitation, Aug. 24-29, 1958.
Grundler, W. et al., Resonant Cellular Effects of Low Intensity Microwaves, in H. Frohlich, editor, Biological Coherence and Response to External Stimuli, Springer-Verlag Publishers, 1988.
Grundler, W. et al., Sharp Resonances in Yeast Growth Prove Nonthermal Sensitivity to Microwaves, *Physical Review Letters*, vol. 51, pp. 1214-1216, Sep. 26, 1983.

(Continued)

Primary Examiner—Marjorie A. Moran

(57) ABSTRACT

Methods are provided for readily and efficiently determining resonant frequencies that can be used therapeutically or beneficially, for debilitation of specific types of genomic materials, including DNA and/or RNA, genes, and gene sections. The methods can be used in a variety of circumstances related to various human and animal diseases and conditions. Methods allow determination of therapeutic resonant frequencies for use in various media having different refractivities. Therapeutic or beneficial resonance frequencies thus determined are adapted for use with currently available frequency-emitting devices by shifting resonant frequencies to electromagnetic ranges capable of generation by such devices.

6 Claims, No Drawings

OTHER PUBLICATIONS

Hakim, M. B. et al., The Speed of Sound in DNA, *Biopolymers*, vol. 12, 1984, pp. 1185-1192.

Hecht, E., Table 17.3, The permittivity ($\epsilon$) and relative permitivitty ($\epsilon/\epsilon_o$) of some common substances, Physics Calculus, vol. Two, p. 664, Brooks/Cole Publishing Co., 1996.

Jacobson, J. I., The Mathematical Framework Essential for Magneto-Therapy in the Treatment of Genomic and Associated Disorders, including Cancer, AIDS, and CNS Regeneration, *Panminerva Medica*, vol. 31, No. 1, pp. 1-7, Jan.-Mar. 1989.

Lide, D. R., editor, CRC Handbook of Chemistry and Physics, 76$^{th}$ Edition, pp. 1-1, 1-5, 1-10, 1-11, & 1-12, CRC Press, Inc., 1995.

Lynes, B., Royal Raymond Rife and the Cancer Cure That Worked!, in Jonathan Eisen, Suppressed Inventions & Other Discoveries, pp. 126-139, Avery Publishing Group, 1999.

Mainguy, J-C. et al., Evolution of Neoplasic Cells in Culture under the Influence of Electromagnetic Fields, *Erfahrungs Heilkunde, Acta Medica Empirical*, pp. 398-404, 1997.

McInturff, B., The Consolidated Annotated Frequency List, www.mindspring.com/~turf/alt/elec/cfl.txt, Oct. 24, 2000.

Pappas, P.T. et al., Effects of Pulsed Magnetic Field Oscillations in Cancer Therapy, invited paper to Int'l Symposium on New Energy sponsored by the Int'l Association for New Science, Apr. 16-18, 1993.

Paulus, A., Bactericidal Radiation, *Journal of Applied Physics*, vol. 13, May 1942.

Postow, E. et al., Modulated Fields and "Window" Effects, in C. Polk et al., Handbook of Biological Effects of Electromagnetic Fields, 2$^{nd}$ ed., pp. 535, 557, 559, 561, and 563, CRC Press, 1996.

Rife, R. R., A Discussion of Laboratory Research, Jun. 14, 1958, www.rife.org/dislabl.html.

Rife, R. R., Culturization of Virus, Jul. 14, 1958, www.rife.org/cultvirus.htm.

Rife, R. R., History of the Development of a Successful Treatment for Cancer and Other Virus, Bacteria and Fungi, Report No. Dev—1042, Allied Industries, 4246 Pepper Drive, San Diego, Calif., Dec. 1, 1953.

Schoenback, K. H. et al., The Effect of Pulsed Electric Fields on Biological Cells: Experiments and Applications, *IEEE Transactions on Plasma Science*, vol. 25, No. 2, pp. 284-292, Apr. 1997.

Shashlov, V. A., On the Mechanism of Frequency-Selective Biological Effects of the EHF Radiation and the Ways to Increase Them, translated from *Izvestiya Vysshikh Uchebaykh Zavedenii, Radiofizika*, vol. 37, No. 1, pp. 103-110, Jan. 1994.

Siedel, R. E. et al., The New Microscopes, Smithsonian Annual Report 1944, pp. 193-220.

Styryer, L.., Biochemistry, 4$^{th}$ Edition, pp. 75-77 and 788, W.H. Freeman and Co., 1995.

Swicord, M. L., Chain-Length-Dependent Microwave Absorption of DNA, *Biopolymers*, vol. 22, pp. 2513-2516, 1983.

The Christchurch Press, Frequency Therapy Offers Relief, Oct. 28, 1999, 1999WL28842371.

Dekker, C and Ratner, M.A., Electronic properties of DNA, Physics World 2001, Aug. 29-33.

Fink, H. and Schonenberger, C., Electrical conduction through DNA molecules, 398 Nature 407-410, Apr. 1, 1999.

The American Heritage Dictionary of the English Language. Boston: Houghton-Mifflin, 2000, p. 734.

Benson, DA et al, "GenBank", Nucleic Acids Research 27 (1): 12- (1999).

Lide, D. ed., CRC Handbook of Chemistry and Physics. Boca Raton: CRC Press, 1995, pp. 1-1, 2-3, 2-4, 12-51.

* cited by examiner

METHODS FOR DETERMINING THERAPEUTIC RESONANT FREQUENCIES

CROSS REFERENCE TO RELATED APPLICATIONS

This application claims priority to applicant's co-pending application having U.S. Ser. No. 60/181,460, filed Feb. 10, 2000.

FIELD OF THE INVENTION

The present invention relates to methods for determining resonant frequencies having therapeutic uses in a variety of settings. In particular, the present invention provides methods for efficiently determining therapeutic resonant frequencies for complete genomes or partial genomic materials, for use in various media having different refractivities.

BACKGROUND OF THE INVENTION

Resonant frequency therapy (RFT) is a non-invasive treatment that has been reported to offer significant relief to sufferers of a variety of ailments and medical conditions. The use of RFT for human and animal therapeutic purposes began in the early 1900's, and experienced accelerated development through the research of Royal Rife and his associates in the 1930's and afterward.

Using new microscope technology he developed, Rife discovered that plasma waves could be used to transmit radio and audio frequencies, which were tuned to the frequencies of specific microorganisms, and that each microorganism responded to its unique frequencies. For example, Rife found that staphylococcus, streptococcus, microorganisms associated with tuberculosis, typhoid, and leprosy, as well as cancer particles, and other disease-causing agents succumbed when exposed to certain frequencies peculiar to each organism or particle. See, Siedel, R. E., and M. E. Winter, The New Microscopes, Smithsonian Annual Report 1944, pp. 193-200.

Using the principles of Rife's discoveries, various researchers developed devices for emitting frequencies designed to treat a range of diseases and conditions. For example, Dr. Abraham Ginsberg used an apparatus which produced intermittent bursts of high energy in the short wave spectrum. Ginsberg's modality was found to stimulate the reticuloendothelial system without undesirably heating tissue. Using his device, Ginsberg reported successfully treating patients with various clinical conditions, including chronic Staphylococcus infections, acute inflammatory middle ear, chronic ulcerative colitis, bronchitis, rheumatoid arthritis, gout, flu, and thrombophlebitis, among others. See, Cominole, B., Clinical Impressions and Speculations on the Use of High-Frequency Pulsed Energy, The Dr. Abraham J. Ginsberg Foundation for Medical Research Symposium, Jun. 29, 1959.

Research utilizing resonant frequencies and therapeutic modalities implementing such frequencies have proliferated over the past ten years. A recent example of the use of resonant frequency therapy is the Christchurch Resonant Frequency Therapy Centre in Dunedin, New Zealand. While the Centre emphasizes that resonant frequency therapy is not intended to replace treatment regimens and medication prescribed by physicians, it does report successful treatment of a range of clinical conditions, including arthritis, tinnitis, blood pressure, cataracts, headaches, shingles, and psoriasis. Arthritis patients report particular success with pain reduction and greater mobility. See The Christchurch Press, Frequency Therapy Offers Relief, Independent Newspapers Limited, Oct. 28, 1999.

Thus, the use of audio, radio, and light waves to inhibit microbial growth and to treat diseases and affected tissue is well known in the art. Effective therapeutic resonant frequencies have been identified through various means. Trial and error approaches with resonant frequencies have been used to obtain therapeutic responses. Devices for applying electromagnetic energy to living tissue are disclosed, for example, in U.S. Pat. Nos. 3,876,373, 4,524,079, and 5,091,152. Effective resonant frequencies have also been identified through the use of frequency scanning with electronic devices capable of detecting a frequency response from a bacterial, viral, and/or tissue sample. Such devices for detecting frequency response are disclosed, for example, in U.S. Pat. Nos. 5,552,274, 5,981,182, and 6,004,257. Thus, there exists a need for more efficient and accurate methodology than trial and error, to determine therapeutic resonant frequencies for specific target materials, such as microorganisms.

Therapeutic resonant frequencies may be used to inhibit, or debilitate, and/or stimulate a biophysical event. The efficacy of such frequencies, whether for stimulation or for debilitation, depends to some extent on the type of frequency delivery system used, including variables such as power levels, waveform, harmonic content of the wave, and other factors. Once therapeutic resonant frequencies are determined, the user must choose which devices and delivery systems are most effectively used in conjunction with those frequencies. To increase efficacy, an easier, quicker, and more accurate way of determining therapeutic resonant frequencies is needed.

Despite both historical and increasing recent interest in use of resonant frequency therapy, mechanism(s) of action underlying the use of known therapeutic resonant frequencies is not fully understood. While it is recognized that some type of resonance phenomenon debilitates or destroys microorganisms, the biophysical and/or biochemical mechanism(s) associated with use of specific resonant frequencies and that lead to microbial inhibition are not completely known.

Before now, there has never existed a methodology that links effective therapeutic resonant frequencies to a biophysical or biochemical event, process, or structure. The electronic scanning devices and methods currently commercially available provide no explanation or insight regarding which physical structure or process is influenced by the frequencies used.

There is a need for methodology to more readily and efficiently influence genomic materials, by more precisely and efficiently determining therapeutic resonant frequencies that can be easily and accurately adjusted to ranges used by currently available devices. It is to these perceived needs that the present invention is directed.

SUMMARY OF INVENTION

The present invention provides methods for determining resonant frequencies having therapeutic uses in a variety of settings. In particular, the present invention provides methods for efficiently and accurately determining therapeutic resonant frequencies for complete genomes and partial genomic materials, for use in various media having different refractivities.

Methods of the present invention utilize biophysical and biochemical properties of genomic materials to determine therapeutic resonant frequencies. For example, the length of any object can be considered as having a resonant frequency by virtue of correlation with a wavelength that manifests itself into a surrounding medium. On that basis, the length of biomolecular chains of DNA and RNA can be calculated, and thus can provide wavelength-matching information unique to a specific strand of genomic material.

DNA or RNA chains are constructed in such a way that negatively-charged molecular ions (the $PO_4$ groups) run the entire length of the molecule on the outer surface of the chain in a helical fashion, causing the molecule to contain a relatively large negative charge on its surface. Thus the chain is highly electro-sensitive to the influences of resonant oscillating electromagnetic fields. Resonance is defined as the increase in amplitude of the natural oscillation or frequency of a system, when exposed to a periodic force whose frequency is equal or very close to the natural frequency of the system. The natural oscillation of a system or part of a system is defined as its "natural resonant frequency".

In radio science, the length of an antenna will largely determine how effectively the antenna responds to the wavelength energy of an incoming transmission. Methods for determining therapeutic resonant frequencies of the present invention utilize the principle that the length of a DNA or RNA helical chain can be electromagnetically resonated in similar fashion.

Methods of the present invention allow precise correlations between resonant frequencies and the length of the genomic material under consideration. If a resonant frequency is generated in air (or a vacuum) while the target material resides in a different medium, in this invention's method a refractive adjustment is made to insure that the wavelength traveling from the air or vacuum medium transforms to the length of the target material in the surrounding medium. By accounting for an appropriate electromagnetic refractive index for the surrounding medium, such as water or tissue, methods of the present invention provide the advantage of determining a resonant frequency that would be more closely related to the length of the genomic material and its natural resonant frequency, and thus would be more appropriate, or therapeutic, for the genomic material in that specific medium.

The natural electromagnetic resonant frequencies for genomes fall for the most part in the infrared region of the electromagnetic (EM) spectrum. The natural resonant frequencies for genes and smaller portions of DNA or RNA appear in the near infrared, visible, and near ultraviolet regions of the spectrum. For many currently available frequency-emitting devices, the natural resonant frequencies such as those associated with genomic material are not achievable due to the technical limitations of the device. Indeed, particular devices often are capable of generating frequencies in only narrow ranges. To overcome such limitations, methods of the present invention adjust resonant frequencies upward or downward. For example, to determine an appropriate lower range frequency in accordance with the present invention, the therapeutic resonant frequency is divided by the number 2, as many times as necessary, until a frequency in the frequency-generating range of a device is reached. The power of 2 by which a therapeutic resonant frequency is factored will depend on the range of the electromagnetic spectrum within which a frequency delivery device operates.

In music, a similar adjustment would be termed moving to a higher or lower octave. Moving to a higher octave would in effect cut the wavelength in half, while moving to a lower octave would double the wavelength. In accordance with methods of the present invention, therapeutic resonant frequencies of genomic material "shifted by octaves," to a lower octave in the electromagnetic spectrum, by dividing the therapeutic resonant frequency by some power of the number 2. The lower octave of a therapeutic resonant frequency, while having a much longer wavelength, will resonate with the first therapeutic resonant frequency, just as musical octaves resonate with and amplify each other, but only when the octave shift is exact.

The present invention comprises methods for determining therapeutic resonant frequencies of electromagnetic radiation for influencing a target genomic material, where the genomic material is surrounded by a medium. Embodiments of these methods include the following steps: (1) determining a velocity of electromagnetic radiation through the medium surrounding the genomic material; (2) determining the length of the genomic material; (3) determining a first resonant frequency of the genomic material in one electromagnetic frequency range by dividing the velocity of the electromagnetic radiation through the surrounding medium by the length of the genomic material; (4) dividing or multiplying the first resonant frequency by a factor of a power of two to obtain at least one resonant frequency in another electromagnetic frequency range; (5) programming a frequency-emitting device to emit at least one resonant frequency in the other electromagnetic frequency range selected in step 4; and (6) selectively influencing the target genomic material with at least one resonant frequency in the selected electromagnetic frequency range, when the frequency-emitting device emits at least one resonant frequency in the selected electromagnetic frequency range into the medium surrounding the target genomic material.

Methods of the present invention further comprise determining the length of the genomic material by determining the number of base pairs in the genomic material (in the case of single-stranded genomic material, this step would comprise determining the number of bases); using the spacing between adjacent base pairs or bases; and multiplying the number of base pairs or bases in the genomic material by the spacing between adjacent base pairs or bases. In a preferred embodiment, the base pairs or bases are spaced apart by an average spacing, which is a known value, and determining the length of the genomic material comprises determining the number of base pairs or bases in the genomic material, and then multiplying that number of base pairs or bases in the genomic material by the known value for the average spacing between base pairs or bases.

In a typical environment, genomic material exists in living, or in-vivo, tissue. In methods of the present invention, the velocity of electromagnetic radiation through in-vivo tissue is determined by accounting for the electrical permittivity of in-vivo tissue in relation to velocity, such that the velocity=$1/\sqrt{(\epsilon\mu)}$, where $\epsilon$ is the electrical permittivity of in-vivo tissue, and $\mu$ is the magnetic permeability of in-vivo tissue. With this measurement of in-vivo velocity, a refractive index of electromagnetic radiation through in-vivo tissue is determined by dividing the velocity of electromagnetic radiation, or the speed of light in a vacuum, by the speed of light in in-vivo tissue. Then by dividing a therapeutic resonant frequency determined for the genomic material in an air medium by the refractive index for in-vivo tissue, a therapeutic resonant frequency for the genomic material surrounded by in-vivo tissue is determined.

In other embodiments, methods of the present invention include multiplying therapeutic resonant frequencies in a range adaptable for use in frequency-emitting devices by a positive integer to determine harmonic frequencies; or dividing therapeutic resonant frequencies in a range adaptable for use in frequency-emitting devices by a positive integer to determine subharmonic frequencies. By programming a frequency-emitting device to emit the harmonic and subharmonic frequencies, target genomic material is selectively influenced with the therapeutic resonant frequencies and the harmonic and subharmonic frequencies, when the frequency-emitting device emits these frequencies into the medium surrounding the target genomic material.

Features of methods for determining therapeutic resonant frequencies of the present invention may be accomplished singularly, or in combination, in one or more of the embodiments of the present invention. As will be appreciated by those of ordinary skill in the art, the present invention has wide utility in a number of applications as illustrated by the variety of features and advantages discussed below.

Methods of the present invention provide numerous advantages over prior efforts to identify therapeutic resonant frequencies. For example, the present invention advantageously provides methods for determining resonant frequencies effective for stimulation and/or debilitation of specific types of DNA and/or RNA genomes, genes and gene sections.

Another advantage of the methods of the present invention is that they provide means for readily and efficiently determining therapeutic resonant frequencies using widely available data.

Another advantage is that the present invention provides methods for readily and efficiently predicting resonant frequencies that can be used therapeutically or beneficially in a variety of circumstances related to treatment of various human and animal diseases and conditions.

Another advantage is that the present invention provides methods for readily and efficiently determining therapeutic resonant frequencies that take into account an appropriate electromagnetic refractive index for a surrounding medium. In so doing, the present invention has the advantage of determining a more precise therapeutic resonant frequency for the genomic system in a particular medium.

Still another advantage is that the present invention provides easier and more efficient methods for determining resonant frequencies that significantly enhance the therapeutic benefit and cost-effectiveness of currently existing electromagnetic, magnetic, plasma, audio, or other frequency-emitting devices.

Another advantage over prior approaches to identifying resonant frequencies is that the present invention provides the advantage of methods that utilize a simple biophysical model for explaining and understanding why specific resonant frequencies are effective.

As will be realized by those of skill in the art, many different embodiments of methods for determining therapeutic resonant frequencies according to the present invention are possible. Additional uses, objects, advantages, and novel features of the invention are set forth in the detailed description that follows and will become more apparent to those skilled in the art upon examination of the following or by practice of the invention.

DETAILED DESCRIPTION OF THE INVENTION

The present invention comprises methods for determining resonant frequencies having therapeutic or beneficial uses in a variety of settings. In particular, the present invention includes methods for efficiently and accurately determining therapeutic resonant frequencies for specific complete genomes, or partial genomic materials. Methods of the present invention also comprise means for determining a more precise, and thus more therapeutic resonant frequency for the genomic system in a particular medium by accounting for an appropriate electromagnetic refractive index for the surrounding medium.

Complete Genome

As described above, an object has a natural resonant frequency by the correlation of the length of the object with a wavelength that manifests into its surrounding medium. For example, the length of a DNA or RNA chain provides a wavelength measurement that can be used to determine a resonant frequency. In embodiments of the present invention, the spacing of nucleotide base pairs in a DNA double helix is used in the mathematical process to determine frequency. The entire length of a piece of genomic material, is determined by multiplying the number of base pairs or bases in the genomic material times the spacing length between base pairs or bases.

It is known that base pair spacing in strands of DNA is not always consistent. Localized areas contain "squeezing" or "spreading" of base pairs in various ways. In embodiments of the methods of the present invention, the classic Watson-Crick model of base pair spacing is used. The Watson-Crick model of base pair spacing is an average spacing over the entire length of the DNA molecule. Use of an average base pair spacing allows for accuracy sufficient to determine therapeutic resonant frequencies in accordance with the methods of the present invention.

The B-helix is the most common in-vivo DNA form in bacterial and eukaryotic life forms, and is used herein as illustration in the methods of the present invention. In the B-helix, one complete turn of the helix spans a distance of 35.4 angstroms on its axis; and there are 10.4 base pairs in each helical turn. Therefore, the spacing of individual base pairs on the axis would be 35.4 angstroms per turn divided by 10.4 base pairs per turn, which equals 3.403846 angstroms spacing between each base pair. In scientific notation using SI units, the base pair spacing length is expressed as 3.403846 e−10 meters. This use of meters allows conversion of the total length (treated as wavelength) into a frequency.

By way of illustration using a pathogenic microorganism, the DNA genome of *Borrelia burgdorferi* strain B31 contains 910,724 base pairs. To determine its length, 910,724 base pairs times the base pair spacing of 3.403846 e−10 meters=3.09996 e−4 meters total length of the genome. As described above, the length of an object can represent the object's wavelength; in this case, the length of the *Borrelia* genome represents its wavelength.

To convert this wavelength to frequency, the following common physics relationship is used:

$$\text{velocity/wavelength}=\text{frequency} \quad (1)$$

If the DNA under consideration was in a medium of air, velocity would be the speed of electromagnetic radiation, or light, in air. For purposes of comparison, if *Borrelia burgdorferi* was in an air medium, according to methods of the present invention, the velocity of electromagnetic radiation through air (299,792,458 m/s) would be used in determining a therapeutic resonant frequency. Dividing this velocity by the *Borrelia burgdorferi* genome wavelength: (299,792,458 m/s/3.09996 e−4 meters)=9.6708492 e+11 Hz, the therapeutic resonant frequency for *Borrelia burgdorferi* in an air medium.

However, genomic material including that of *Borrelia burgdorferi*, generally exists in a medium of living tissue.

The velocity of electromagnetic radiation through a general in-vivo tissue medium is equal to the inverse of the square root of the product of the electrical permittivity and the magnetic permeability of the medium. The formula for velocity of electromagnetic radiation through a typical in-vivo tissue medium is given as:

$$\text{velocity} = 1/\sqrt{(\epsilon\mu)} \quad (2)$$

where $\epsilon$ is the electrical permittivity and $\mu$ is the magnetic permeability of the medium.

The magnetic permeability ($\mu$) through in-vivo tissue is known to be the same as that in air: 1.256,637,061,4 e−6 henrys/meter. However, electrical permittivity in live body tissue is not the same as for air. A representative value for electrical permittivity through in-vivo tissue is 71 e−12 farads/meter. Applying these figures to formula (2) above, the result is: velocity=$1/\sqrt{[(71\text{ e}-12\text{ F/m})\times(1.256,637,061,4\text{ e}^{-6}\text{ H/m})]}$=105,868,288.9 meters per second, a representative velocity of electromagnetic radiation through in-vivo tissue.

Thus, in this method of the present invention, to obtain an in-vivo therapeutic resonant frequency of the *Borrelia burgdorferi* DNA genome having a length of 3.09996 e−4 meters, formula (1) above (velocity/wavelength=frequency) is used: 105,868,288.9 meters per second/3.099,96 e−4 meters=3.415,150,16 e+11 Hz.

Using the results of the above steps, a general refractive index of electromagnetic radiation through in-vivo tissue can be determined. A refractive index (n) is given by the ratio of the speed of light in a vacuum to the speed of light in the medium under consideration. This ratio is stated as:

$$n = \text{speed of light in a vacuum/speed of light in a medium.} \quad (3)$$

According to the steps given above, a refractive index of electromagnetic radiation through in-vivo tissue would be: (299,792,458 m/s)/(105,868,288.9 m/s)=2.831749.

Then, by dividing a therapeutic frequency determined for a particular genomic material in an air medium by the refractive index for in-vivo tissue, a therapeutic resonant frequency for the genomic material in an in-vivo tissue medium is quickly determined. Following the example above, dividing the resonant frequency of *Borrelia* in air (9.6708492 e+11 Hz) by the refractive index of electromagnetic radiation through in-vivo tissue (2.831,749), gives the in-vivo resonant frequency for the *Borrelia burgdorferi* genome (3.41515016 e+11 Hz).

The steps described above for the methods of the present invention can be adjusted to correlate with any medium surrounding the genomic material under consideration, as long as an accurate electromagnetic velocity through the medium is known or can be determined.

The 3.415,150,16 e+11 Hz in-vivo therapeutic resonant frequency determined above for the *Borrelia burgdorferi* genome appears in the infrared range of the electromagnetic spectrum. In embodiments of the present invention, methods allow access to corresponding resonant frequencies in the lower audio range. For example, to determine an accurate resonant frequency in the audio range corresponding to first therapeutic resonant frequency, the first resonant frequency is divided by the number 2, as many times as necessary, to reach a frequency in the audio range. In musical terms, as described above, frequencies that are related by a factor of 2, or a power thereof, are known as octaves. In the example of the in-vivo *Borrelia burgdorferi* genome, a multi-octave shift to audio range can be reached by dividing the first therapeutic resonant frequency by $2^{29}$, which gives a corresponding second therapeutic resonant frequency of 636.12 Hz, which is in the audio range. This process of dividing (or multiplying) any resonant frequency transposes it into a different octave by doubling (or halving) its wavelength in an exact and precise manner, allowing a resonant correlation with the length under consideration in a specific medium. Thus, in the present invention, an octave-shifted therapeutic resonant frequency will have a precise correlation with the first therapeutic resonant frequency.

In the example above, an in-vivo therapeutic resonant frequency of the *Borrelia burgdorferi* genome is 3.41515016 e+11 Hz. Corresponding therapeutic useful resonant frequencies in a different electromagnetic range, determined by dividing by appropriate powers of 2, results in *Borrelia burgdorferi* in-vivo therapeutic resonant frequencies in the audio range at: 636.12 Hz, 1272.24 Hz, 2544.5 Hz, 5088.9 Hz, etc.

As another illustration, if *Borrelia burgdorferi* were in a different medium such as water at 40 degrees centigrade, according to methods of the present invention, the velocity of EM radiation through water at that temperature (225,319,768 m/s) would be used in determining therapeutic resonant frequencies. Dividing this velocity by the genome length: (225,319,768 m/s)/(3.09996 e−4 meters)=7.2684734 e+11 Hz, which would be the therapeutic resonant frequency of *Borrelia burgdorferi* DNA in water at 40 degrees centigrade.

To determine corresponding therapeutic resonant frequencies in a different electromagnetic frequency range, again in this instance the audio range, the resulting resonant frequency above is then divided by appropriate powers of 2. This gives therapeutic resonant frequencies in the audio range for *Borrelia burgdorferi* in a 40-degree centigrade water medium of: 676.9 Hz, 1353.9 Hz, 2707.7 Hz, 5415.4 Hz, etc.

In an alternative embodiment of the present invention, methods for determining therapeutic resonant frequencies for genomic material under consideration use the numerical constant 4,526,016.44 as follows: 4,526,016.44 divided by the number of base pairs or bases in a chain=frequency. As such, this method provides an efficient means for determining frequency by ascertaining the number of base pairs or bases in the genomic material, and dividing that number into the aforementioned constant. For example, if there are 250 base pairs, or bases in a DNA chain, 4,526,016.44/250=18,104.07 hertz. For 5,000 base pairs or bases in a DNA chain, 4,526,016.44/5,000=905.20 hertz. For 22,000 base pairs or bases in a DNA chain, 4,526,016.44/22,000=205.73 hertz.

As described above, in methods of the present invention, therapeutic resonant frequencies are also determined for a different electromagnetic range, for example in the audio range, by dividing (or multiplying) by appropriate powers of 2. Using the example of a 250-base pair DNA chain above, 18,104.07 Hz/2=9,052.035 Hz. Repeated division of the resulting frequency by a factor of 2, such that 9,052.035 Hz/2=4526.017 Hz/2=2263.008 Hz/2=1131.504 Hz/2=565.752 Hz, quickly determines frequencies in the range capable of generation by typical frequency-emitting devices. To further shorten the process, dividing 18,104.07 hz by 32, or $2^5$ (2 to the power of 5), yields a frequency of 565.752 Hz. Multiplying or dividing by an appropriate factor of 2 (2, 4, 8, 16, 32, 64, 128, 526, etc.) will accurately convert therapeutic resonant frequencies to a desired range for use in currently available frequency emission devices. Shifting frequencies by factors of 2 produces a frequency event that is an octave-related resonant frequency and wavelength.

As described above, many currently available frequency-emitting devices are not capable of producing therapeutic resonant frequencies in the infrared range, as that determined for the *Borrelia burgdorferi* genome. To overcome such limitations, methods of the present invention adjust resonant frequencies downward (or upward) by dividing (or multiplying) by a power of 2, until a frequency in the frequency-generating range of a device is achieved.

Certain frequency devices emit not only a basic frequency (also referred to as the "fundamental" frequency), but also many harmonics of that frequency. A "harmonic" is defined as a positive integer multiple of the fundamental frequency. On this basis, in methods of the present invention, additional frequencies can be determined and programmed into a frequency-emitting device such that a harmonic of a frequency corresponding to a first therapeutic resonant frequency of a target genomic material, would be emitted along with the fundamental frequency. Similar additional frequencies can be determined by dividing the therapeutic resonant frequency by a positive integer, resulting in a "subharmonic" frequency. Subharmonic frequencies corresponding to a first therapeutic resonant frequency of a target genomic material could also be programmed into a frequency-emitting device, and be emitted along with the fundamental frequency. In this manner, a group of resonant frequencies corresponding to the first therapeutic resonant frequency can be emitted simultaneously. As a result, effectiveness of a particular device can be enhanced.

As an example, one in-vivo *Borrelia burgdorferi* therapeutic resonant frequency in an audio-range octave is 636.12 Hz. When this therapeutic resonant frequency is divided by the positive integer 2, the resulting subharmonic frequency is 318.06 Hz. When this subharmonic frequency is programmed into a harmonic-rich output device and emitted, the audio-range therapeutic resonant frequency 636.12 Hz is emitted simultaneously, increasing the likelihood that a therapeutic resonant frequency will impinge a target *Borrelia burgdorferi* genome. In like manner, when dividing the audio-range therapeutic resonant frequency 636.12 Hz by the positive integer 3, the resulting subharmonic frequency is 212.04 Hz. A harmonic-rich output device programmed with this subharmonic frequency would also emit the 636.12 Hz therapeutic resonant frequency, further increasing the likely efficacy of the treatment.

The in-vivo therapeutic resonant frequency determined in the audio range for the *Borrelia burgdorferi* genome (636.12 Hz) is very close to a frequency (640 Hz) commonly used for lyme disease, which is caused by *Borrelia burgdorferi*. The accuracy of the methods of the present invention may be confirmed by comparing the resultant therapeutic resonant frequencies produced by these methods, with many known and publicly available therapeutic frequencies.

In another example using a different pathogen, the Rubella measles RNA virus contains 9755 bases in its entire genome. (9755 nucleotides)×(the spacing of 3.403846 e−10 meters)=3.32045 e−6 meters total length. This length is used as the wavelength for the Rubella viral genome. To obtain the in-vivo therapeutic resonant frequency of this wavelength, formula (1) above is again used: (105,868,288.9 meters per second)/(3.32045 e−6 meters)=3.188371724 e+13 Hz. A shifting of this near-infrared frequency to audio range by dividing by $2^{36}$, gives a frequency of 463.97 Hz. A known therapeutic frequency for the condition of Rubella measles is 459 Hz, which is another close match to the therapeutic resonant frequency determined by the methods of the present invention.

A number of favorable responses have been reported by individuals using previously unknown therapeutic resonant frequencies determined by methods of the present invention. For example, one person who often experienced severe outbreaks of herpes simplex virus used the genome-related therapeutic resonant frequencies derived by the methods of the present invention for several strains of herpes simplex viruses. This individual reported a much faster healing process than what is usually experienced. Another example involves a person suffering from cancerous cervical warts. After use of previously unknown therapeutic resonant frequencies relating to the genome of a strain of papilloma virus derived by the methods of the present invention, this person reported disappearance of the warts. Still another example is a person infected with the chickenpox virus, who used a previously unavailable therapeutic resonant frequency derived by the methods of the present invention and associated with the varicella virus genome. This person reported rapid disappearance of blisters and symptoms associated with this disease.

In addition, in-vitro laboratory testing demonstrated that exposure of a strain of *Escherichia coli* to a genome-related resonant frequency produced a statistically significant reduction in the number of colonies in cultures.

Genes and Gene Sections

Methods of the present invention for determining therapeutic resonant frequencies as described above can also be applied to sections of DNA and/or RNA, as in genes, for example. Using genetic coding information, methods of the present invention for determining therapeutic resonant frequencies may also be utilized with other sub-components of genomic material, such as the coding associated with enzymes, immune factors, oncogenes, oncogenic growth factors, and other proteins.

In embodiments of the present invention, therapeutic resonant frequencies are determined using basic information about a protein, for example, how many amino acids are in the protein chain. Because an amino acid is always coded by three bases in the messenger RNA, the number of bases for use in determining resonant frequencies can be ascertained by multiplying the number of amino acids in a protein chain by 3. For example, if there are 100 amino acids in a protein chain, there would be 300 bases in the final messenger RNA related to that protein. Thus, according to methods of the present invention, a therapeutic resonant frequency can be easily determined: 4,526,016.44/300 bases=15,086.72 Hz. Using a factor of $2^5$ to determine a corresponding therapeutic resonant frequency in a lower octave within the acoustic range as described in the methods of the present invention above, the resulting therapeutic resonant frequency would be: 15,086.72 Hz/32=471.46 Hz. which is a frequency that currently available frequency-emitting devices are capable of generating.

As an example, the int-1 mammary oncogene contains 4522 base pairs of DNA. A therapeutic resonant frequency for this oncogene determined by the methods of the present invention above is 2001.77 Hz. This therapeutic resonant frequency is very close to 2008 Hz, a commonly used cancer-related frequency. Furthermore, the messenger RNA associated with the final form of the transforming protein of the int-1 mammary oncogene contains 1112 bases. A therapeutic resonant frequency for this transforming protein determined by the methods of the present invention above is 2035.08 Hz, which is also in a range of cancer-related frequencies currently in use.

As another example, the messenger RNA for the cancer-associated enzyme human tyrosine kinase contains 3151 bases. A therapeutic resonant frequency for this enzyme's messenger RNA, as determined by the methods of the present invention above, is 2872.7 Hz. This frequency is very close to the cancer-related frequency 2876 Hz, which, along with its related octaves, have been used throughout most of the twentieth century in association with certain cancer therapy modalities.

Another example is a precursor gene for *Borrelia burgdorferi* outer surface protein A (ospA), which contains 822 base pairs. A therapeutic resonant frequency for this gene determined by the methods of the present invention above, after being factored by powers of 2 to the audible range, is 344.13 Hz. A previously known frequency currently used for therapy related to lyme disease is 344 Hz, nearly an exact match.

As can be seen, therapeutic resonant frequencies for genes, gene sections, and constituent components of genomic material can be determined more readily and efficiently by methods of the present invention than for example, by trial and error.

Favorable responses have been reported from the use of previously unavailable therapeutic resonant frequencies determined by methods of the present invention, relating to genes, components of genes, and/or messenger RNA coding associated with certain proteins. For example, an individual diagnosed with lung cancer used therapeutic resonant frequencies related to certain growth factors and the K-ras oncogene, which is associated with his type of tumor. It is reported that this individual experienced eradication of lung tumor material. Another example is a student experiencing symptoms of both lyme disease and ehrlichiosis, who was unable to attend school for a year and half due to the severity of symptoms. The student used previously unavailable therapeutic resonant frequencies as determined by methods of the present invention, for certain membrane and antigenic proteins associated with the organism *Ehrlichia chaffeensis*. Within two weeks of beginning therapy with those therapeutic resonant frequencies, this student was well enough to return to school.

While the present invention has been described with reference to several specific embodiments, those skilled in the art will be able to make various modifications to the described embodiments, for instance, by factoring therapeutic resonant frequencies to electromagnetic ranges to other than audible ranges, and by adjusting for various media, without departing from the spirit and scope of the invention. It is therefore to be understood that within the scope of the appended claims the invention may be practiced other than as specifically described herein.

What is claimed is:

1. A method for determining therapeutic resonant frequencies of electromagnetic radiation for treating an animal or human infected with a disease caused by a pathogen, wherein said pathogen comprises a genomic material, the genomic material being surrounded by a medium, comprising:

providing a frequency-emitting device;

determining a velocity of the electromagnetic radiation through the medium surrounding the genomic material;

determining the length of the genomic material;

determining a first therapeutic resonant frequency to influence the genomic material in a first electromagnetic frequency range, by dividing the velocity of the electromagnetic radiation through the medium surrounding the genomic material by the length of the genomic material;

dividing or multiplying the first therapeutic resonant frequency by a factor of a power of two, to obtain a second therapeutic resonant frequency to influence said genomic material, wherein the second therapeutic resonant frequency is in an electromagnetic frequency range capable of being emitted by the frequency-emitting device;

programming the frequency-emitting device to emit the first, or the second resonant frequency; and treating the animal or human with the programmed resonant frequency intended to influence said genomic material, thereby rendering a therapeutic or desirable effect in the animal or human.

2. The method of claim 1, wherein determining the length of the genomic material comprises using the known spacing value between adjacent base pairs or bases, determining the number of base pairs or bases in the genomic material, and multiplying the number of base pairs or bases in the genomic material by the known spacing value between adjacent base pairs or bases.

3. The method of claim 1, wherein the medium surrounding the genomic material has electrical permittivity and magnetic permeability, wherein determining the velocity of the electromagnetic radiation through the medium surrounding the genomic material comprises relating the electrical permittivity and magnetic permeability to the velocity, wherein the velocity=$1/\sqrt{(\epsilon\mu)}$, where $\epsilon$ is the electrical permittivity of the medium, and $\mu$ is the magnetic permeability of the medium.

4. The method of claim 1, further comprising the steps of:

dividing at least one of the previously calculated resonant frequencies by a positive integer to determine subharmonic frequencies, or multiplying at least one of the previously calculated resonant frequencies by a positive integer to determine harmonic frequencies;

additionally programming the frequency-emitting device to emit one or more of the said subharmonic or harmonic frequencies, and treating the animal or human with one or more of the said subharmonic or harmonic frequencies.

5. The method of claim 4, wherein treating a human with the said first or second resonant frequency, or one of the said subharmonic or harmonic frequencies, comprises influencing said genomic material present in humans.

6. The method of claim 4, wherein treating an animal with the said first or second resonant frequency, or one of the said subharmonic or harmonic frequencies, comprises influencing said genomic material present in animals.

* * * * *